United States Patent
Lu et al.

(10) Patent No.: US 11,338,049 B1
(45) Date of Patent: May 24, 2022

(54) ULTRAVIOLET STERILIZING BOX STRUCTURE

(71) Applicant: HERGY INTERNATIONAL CORP., Taipei (TW)

(72) Inventors: Chun-Hung Lu, Taipei (TW); Chia-Te Lin, Taipei (TW); Chih-Hsin Chen, Taipei (TW)

(73) Assignee: HERGY INTERNATIONAL CORP., Taipei (TW)

( * ) Notice: Subject to any disclaimer, the term of this patent is extended or adjusted under 35 U.S.C. 154(b) by 69 days.

(21) Appl. No.: 16/953,390

(22) Filed: Nov. 20, 2020

(51) Int. Cl.
| | | |
|---|---|---|
| *A61L 2/10* | (2006.01) | |
| *A61L 2/26* | (2006.01) | |
| *A61L 9/20* | (2006.01) | |
| *C02F 1/32* | (2006.01) | |
| *A61L 2/00* | (2006.01) | |

(52) U.S. Cl.
CPC .............. *A61L 2/10* (2013.01); *A61L 2/0047* (2013.01); *A61L 2/26* (2013.01); *A61L 9/20* (2013.01); *C02F 1/325* (2013.01); *A61L 2202/11* (2013.01); *A61L 2202/122* (2013.01); *A61L 2202/123* (2013.01); *A61L 2209/12* (2013.01); *C02F 2201/3222* (2013.01); *C02F 2201/3228* (2013.01); *C02F 2303/04* (2013.01)

(58) Field of Classification Search
CPC . A61L 2/10; A61L 2/26; A61L 2/0047; A61L 9/20; A61L 2202/11; A61L 2202/122; A61L 2202/123; A61L 2209/12; C02F 1/325; C02F 2201/3222; C02F 2201/3228; C02F 2303/04

USPC ...................................... 250/455.11
See application file for complete search history.

(56) References Cited

U.S. PATENT DOCUMENTS

| | | | | |
|---|---|---|---|---|
| 2008/0136191 | A1* | 6/2008 | Baarman | F03B 3/04 290/54 |
| 2009/0145855 | A1* | 6/2009 | Day | C02F 1/325 210/748.14 |
| 2009/0294688 | A1* | 12/2009 | Evans | A23L 3/28 250/436 |
| 2015/0053624 | A1* | 2/2015 | Maiden | C02F 1/002 210/748.11 |
| 2020/0339438 | A1* | 10/2020 | Lautzenheiser | C02F 1/006 |

FOREIGN PATENT DOCUMENTS

WO 2013086274 A1 6/2013

OTHER PUBLICATIONS

Taiwanese Office Action in corresponding Taiwanese Application No. 109134434, dated Mar. 16, 2021.

* cited by examiner

*Primary Examiner* — Kiet T Nguyen
(74) *Attorney, Agent, or Firm* — Bacon & Thomas, PLLC

(57) ABSTRACT

The invention is a UV sterilizing box structure. A box body has a round chamber, an inlet, and an outlet. The round chamber is formed with an arc-shaped guiding channel. A UV light module is disposed on a side of the box body. An external fluid enters the round chamber via the inlet and spirally flows through an inside of the round chamber along the arc-shaped guiding channel so as to make the fluid in the box body generate a flow with a specific direction and stay for enough time to be sufficiently irradiated by UV rays. Thereby, a better effect of sterilization may be obtained.

10 Claims, 5 Drawing Sheets

ULTRAVIOLET STERILIZING BOX STRUCTURE

BACKGROUND OF THE INVENTION

Technical Field

The invention relates to a UV sterilizing equipment, particularly relates to a UV sterilizing box structure.

Related Art

Currently, the devices with ultraviolet (UV) lamps (such as a UV light tube or LED) for sterilizing fluid such as water or air are already in the market. A UV lamp is arranged inside or outside a box and a single flow channel is used to have fluid being irradiated by UV rays. Thereby sterilization can be accomplished by irradiating the fluid with UV rays.

In a conventional sterilizing box structure, the flow channel is lengthened to prolong the irradiating time. However, the volume is also increased. Also, the flow channel is flattened to decrease the irradiating distance for better effect of sterilization. However, the flow resistance is increased and the flowrate is reduced.

In view of this, the inventors have devoted themselves to the above-mentioned prior art, researched intensively and cooperated with the application of science to try to solve the above-mentioned problems. Finally, the invention which is reasonable and effective to overcome the above drawbacks is provided.

SUMMARY OF THE INVENTION

An object of the invention is to provide a UV sterilizing box structure, which arranges the inlet and outlet at different sides of the box body, forms a guiding channel on an inner wall of the box body, and makes the fluid in the box body spirally flow under the principle of inertia, so that the fluid may stay for a longer time in the chamber to avoid the fluid being last in first out to guarantee sufficient UV irradiation. Also, the chamber of the invention may reduce system flow resistance. Sufficient flowrate may be obtained with lower water entering pressure. A better effect of sterilization and sufficient flowrate may be achieved to increase the utility of the invention.

To accomplish the above object, the invention is an ultraviolet (UV) sterilizing box structure, which includes a box body and a UV light module. The box body has a round chamber, an inlet, and an outlet. Both the inlet and the outlet connect with the round chamber. An inner wall of the round chamber is formed with an arc-shaped guiding channel. The inlet is located on a bottom of a side of the box body and connects with the arc-shaped guiding channel. The outlet is located on a middle of another side of the box body. The UV light module is disposed on a side of the box body. The UV light module includes a circuit board, an UV LED (light emitting diode) electrically connected to the circuit board and a light-permeable element covering the UV LED, UV rays emitted by the UV LED entering the round chamber through the light-permeable element. An external fluid enters the round chamber via the inlet, spirally flows through an inside of the round chamber along the arc-shaped guiding channel, and flows out of the outlet after being irradiated by the UV rays of the UV LED.

In comparison with the conventional structure, the UV sterilizing box of the invention arranges the inlet and the outlet at different sides of the box body in a perpendicular manner. Besides, the box body has a round chamber and an inner wall of the round chamber is formed with an arc-shaped guiding channel. Thus, the fluid flowing into the round chamber is guided by the arc-shaped guiding channel and slowly and spirally flows toward the inside of the round chamber under the principle of inertia to compress the water in the round chamber. Further, the compressed fluid is accelerated to flow out of the outlet at the other side of the box body. Accordingly, the staying time of the fluid in the box body is increased to avoid the fluid being last in first out. The fluid is uniformly and sufficiently irradiated by UV rays of the UV LED to accomplish sterilization and the utility of the invention is increased. Also, the fluid in the UV sterilizing box of the invention flows into the chamber instead of a thin and long flow channel. The conventional sterilizing box with a thin and long flow channel may increase the system flow resistance and decrease the utility. Comparing to the conventional sterilizing box, the flow-out rate is lower in this invention. Thus, the requirement of structural force is decreased and the utility in use is increased in this invention.

DETAILED DESCRIPTION OF THE INVENTION

To further disclose the features and technical contents of the invention, please refer to the following description and the drawings. However, the drawings are used for reference and description only, not for limitation to the invention.

Figure 1:
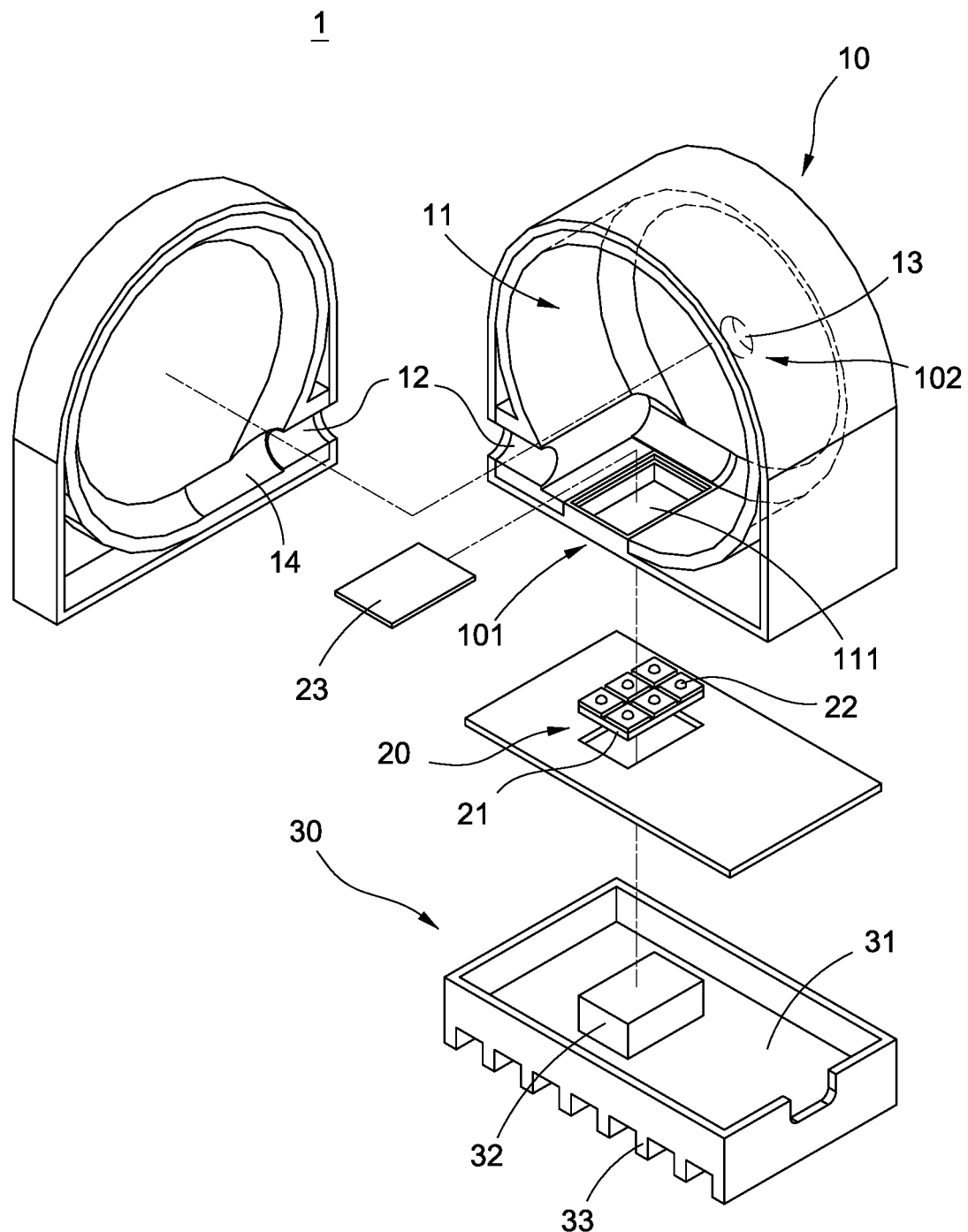
FIG. 1 is an exploded view of the UV sterilizing box structure of the invention.
Figure 2:
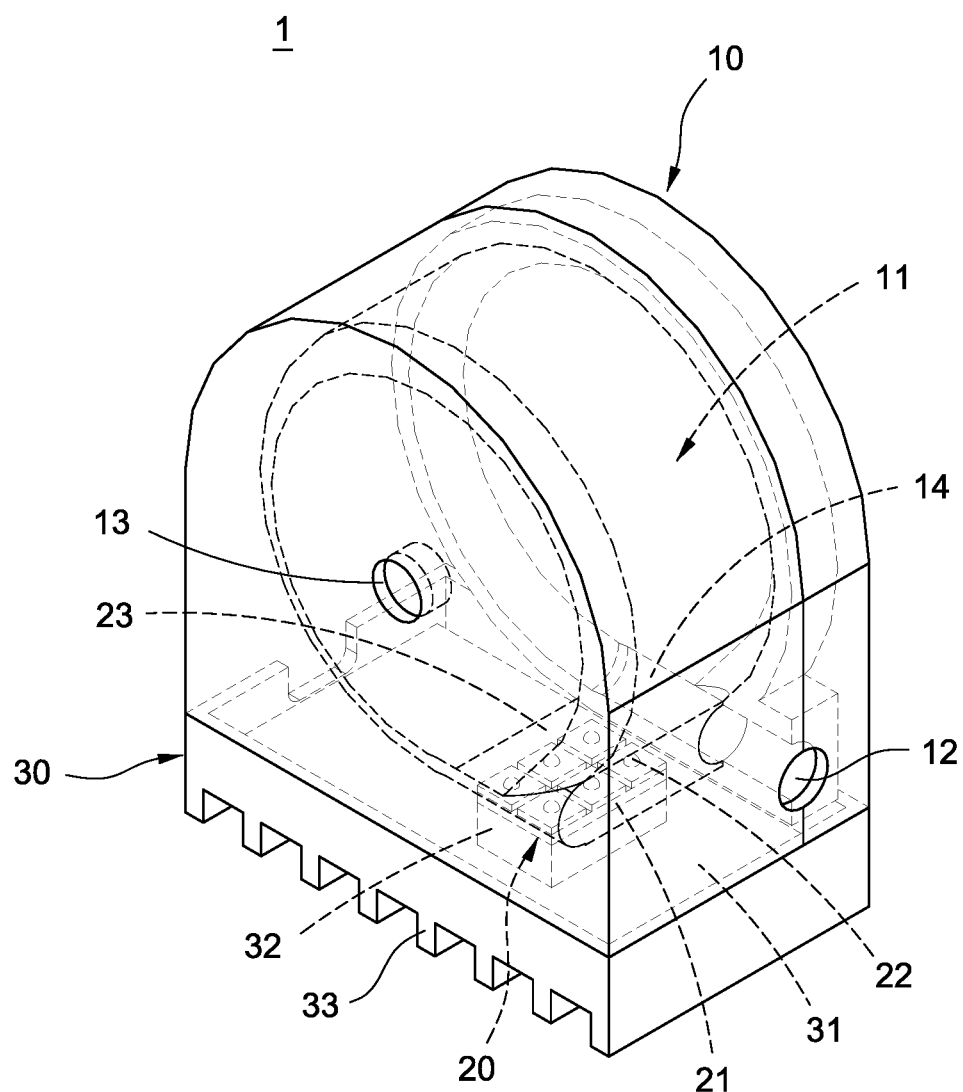
FIG. 2 is a perspective schematic view of the UV sterilizing box structure of the invention.
Figure 3:
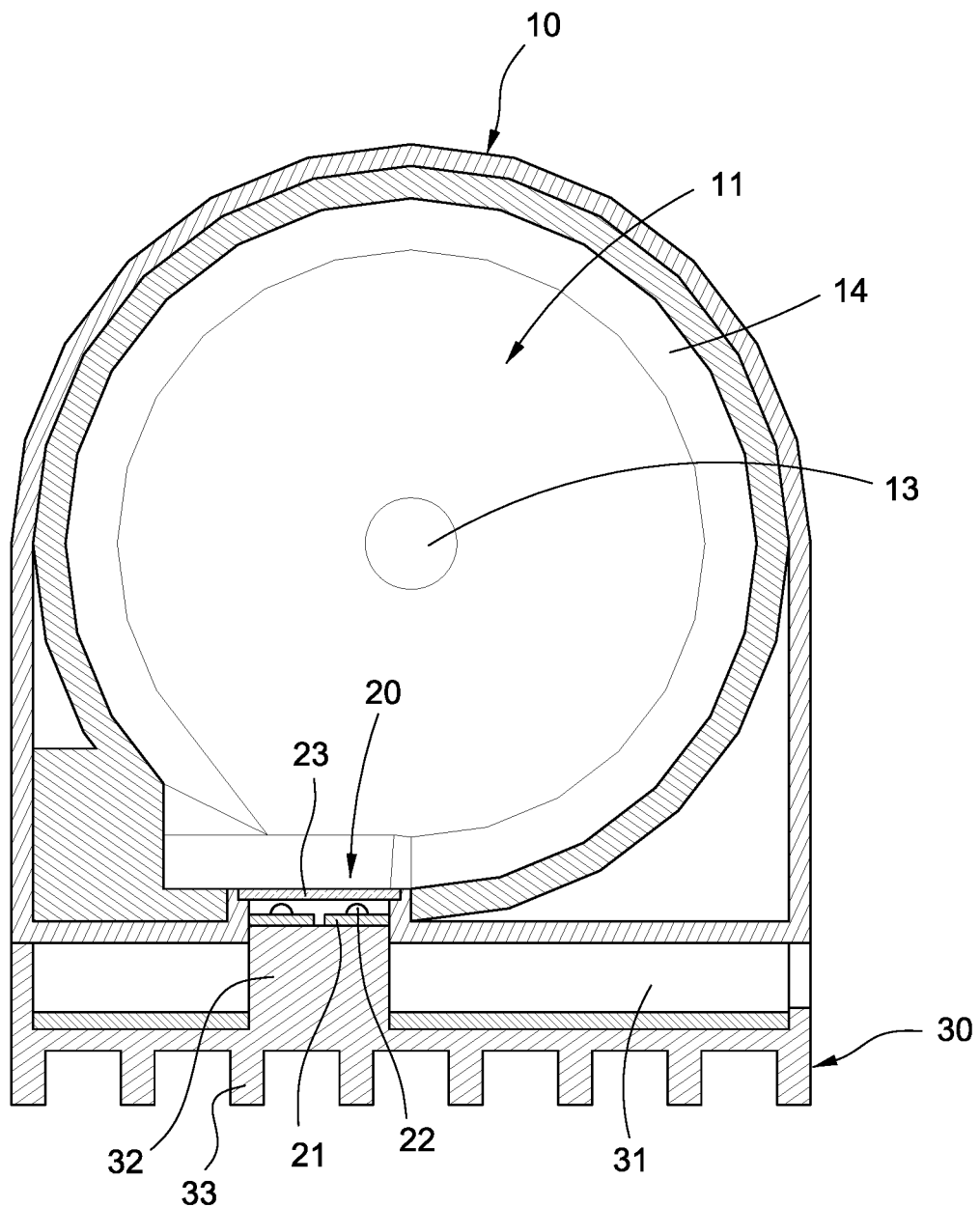
FIG. 3 is a cross-sectional view of the UV sterilizing box structure of the invention.

Please refer to FIGS. 1-3, which are an exploded view, a perspective schematic view and a cross-sectional view of the UV sterilizing box structure of the invention. The invention is an ultraviolet (UV) sterilizing box structure, which includes a box body 10 and a UV light module 20 connected with the box body 10. UV rays emitted by the UV light module 20 irradiate the fluid in the box body 10 to accomplish the effect of sterilization to the fluid in the box body 10. The detailed description of the UV sterilizing box structure is described as below.

The box body 10 has a round chamber 11, an inlet 12 and an outlet 13. Both the inlet 12 and the outlet 13 connect (or communicate) with the round chamber 11. An inner wall of the round chamber 11 is formed with an arc-shaped guiding channel 14. The inlet 12 is located on a bottom 101 of a side surface of the box body 10 and connects with the arc-shaped guiding channel 14. The outlet 13 is located on a middle 102 of another side surface of the box body 10. A normal direction of the outlet 13 is perpendicular to a normal direction of the inlet 12.

It should be noted that the arc-shaped guiding channel 14 is disposed as tapering off toward the inside of the round chamber 11 for forming a spiral shape. In an embodiment of the invention, a shape of the box 10 is of a substantially cylindrical shape.

The UV light module 20 is disposed on a side of the box body 10. The UV light module 20 includes a circuit board 21, a UV LED (light emitting diode) 22 and a light-permeable element 23. The UV LED 22 is electrically connected to the circuit board 21. The light-permeable element 23 covers the UV LED 22 and makes UV rays emitted by the UV LED 22 enter the round chamber 11. In other words, UV rays emitted by the UV LED 22 may enter the round chamber 11 through the light-permeable element 23.

In detail, the box body 10 is provided with a recess 111 on the bottom of the round chamber 11. The UV LED 22 is located in the recess 111. The light-permeable element 23 may be a light-permeable plate. The light-permeable element 23 is fixed (or disposed) on a top portion of the recess 111 and covers the UV light module 20.

In this embodiment, preferably, the UV sterilizing box 1 further includes a heat sink 30. The heat sink 30 is connected to the box body 10 and abuts against the circuit board 21 for heat dissipation to the circuit board 21.

In detail, the heat sink 30 has an accommodating space 31. A heat conducting block 32 is disposed in the accommodating space 31. The circuit board 21 is disposed on the heat conducting block 32. Also, a side surface of the heat sink 30, which is located away from the box body, is formed with multiple fins 33. Thus, the heat generated from the UV light module 20 during operation may be conducted through the heat conducting block 32 and dissipated by the fins 33.

Figure 4:
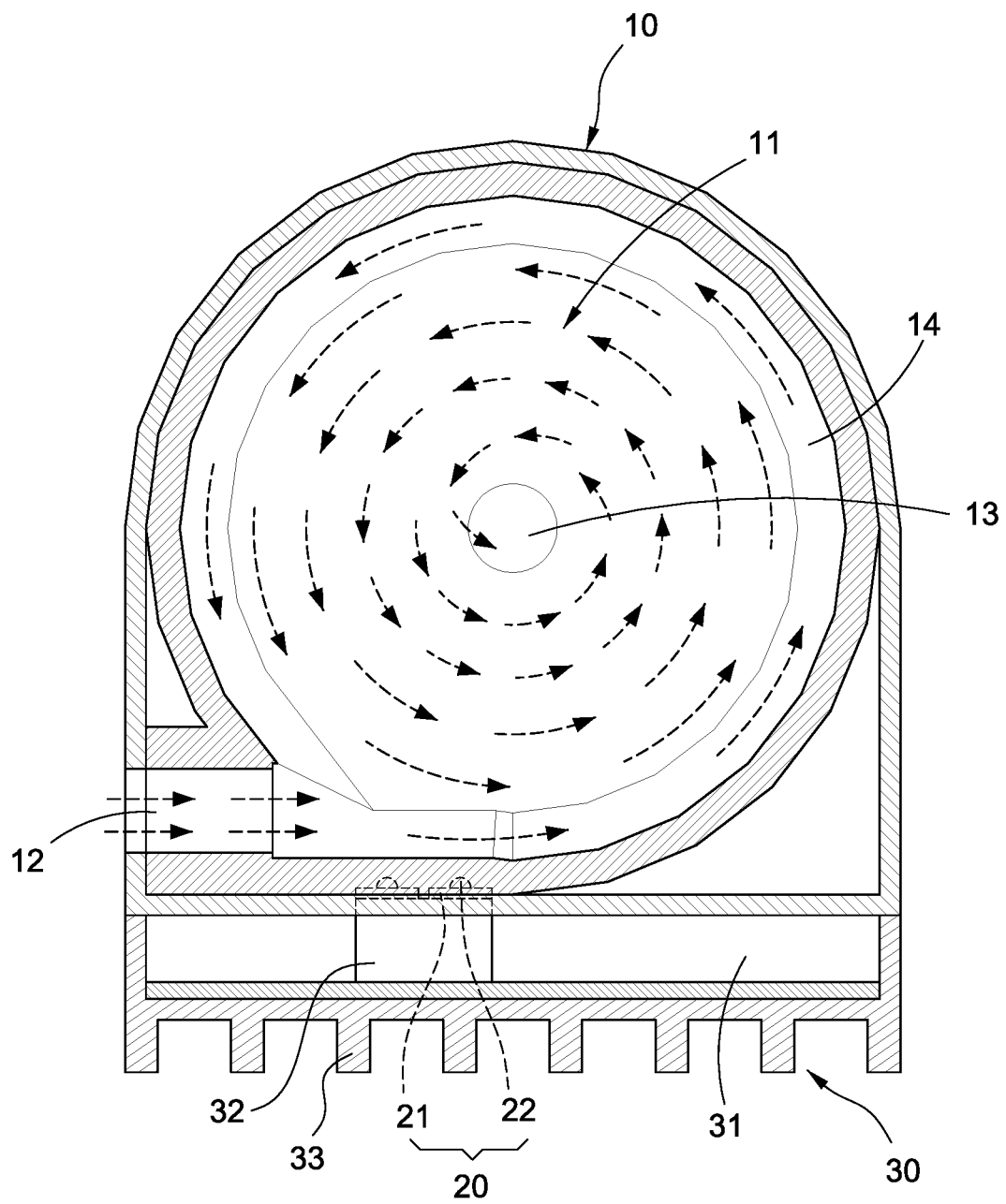
FIG. 4 is a schematic view of the UV sterilizing box structure of the invention in use.

Please refer to FIG. 4, which is a schematic view of the UV sterilizing box structure of the invention in use. When the UV sterilizing box structure of the invention is used, an external fluid enters the round chamber 11 via the inlet 12, slowly and spirally flows toward the inside of the round chamber 11 along the arc-shaped guiding channel 14 under the principle of inertia, and flows out of the outlet 13 after being irradiated by the UV rays of the UV LED 22.

After the external fluid enters the round chamber 11 via the inlet 12 on the bottom 101 of a side surface of the box body 10, the speed of the fluid is fast and the fluid is guided by the arc-shaped guiding channel 14. The fluid slowly and spirally flows toward the inside of the round chamber 11 along the arc-shaped guiding channel 14 under the principle of inertia to compress the fluid in the round chamber 11. The compressed fluid is accelerated to flow out of the outlet 13 on another side. Thus, the staying time of the fluid in the box body 10 may be increased and the fluid may be irradiated with sufficient UV under sufficient time. The fluid is uniformly and sufficiently irradiated by UV rays of the UV LED 22 to accomplish the effect of sterilization.

Figure 5:
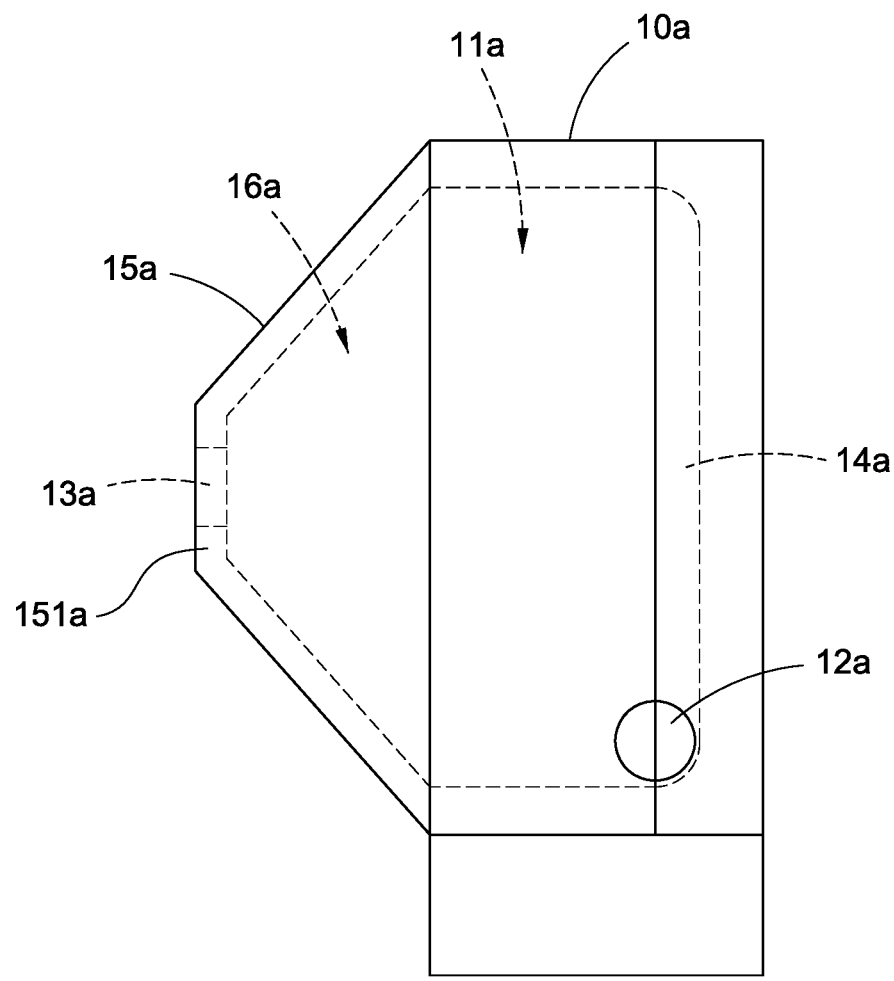
FIG. 5 is a schematic view of the UV sterilizing box structure according to another embodiment of the invention.

Please refer to FIG. 5, which is a schematic view of the UV sterilizing box structure according to another embodiment of the invention. The shape of the box body 10a of the UV sterilizing box 1a is not limiting. As shown in FIG. 5, in this embodiment, the box body 10a has a round chamber 11a, an inlet 12a and an outlet 13a. An inner wall of the round chamber 11a is formed with an arc-shaped guiding channel 14a.

The difference of this embodiment is that a conic shell 15a is formed on an opposite side from the arc-shaped guiding channel 14a and the outlet 15a is disposed on the conic shell 15a. The conic shell 15a has a conic chamber 16a and a flat top 151a. The conic chamber 16a is communicated with the round chamber 11a. In other words, the conic chamber 16a and the round chamber 11a collectively form an accommodating chamber. The outlet 13a is located on the flat top 151a.

The box body 10a disposing with the conic shell 15a may let the fluid slowly rotate in the round chamber 11a and the conic chamber 16a in a spiral manner. The compressed fluid is accelerated to flow out of the outlet 13a on the conic shell 15a. Thus, the fluid in the box body 10a may be irradiated by UV under sufficient time to accomplish the effect of sterilization.

It will be appreciated by persons skilled in the art that the above embodiments have been described by way of example only and not in any limitative sense, and that various alterations and modifications are possible without departure from the scope of the invention as defined by the appended claims.

What is claimed is:

1. An ultraviolet (UV) sterilizing box structure comprising:
   a box body, comprising a round chamber, an inlet and an outlet, both the inlet and the outlet communicating with the round chamber, wherein an arc-shaped guiding channel is disposed on an inner wall of the round chamber, the inlet is located on a bottom of a side surface of the box body and connected with the arc-shaped guiding channel, and the outlet is located on a middle of another side surface of the box body; and
   a UV light module, disposed on a side of the box body, comprising a circuit board, a UV LED (light emitting diode) electrically connected to the circuit board and a light-permeable element covering the UV LED, UV rays emitted by the UV LED entering the round chamber through the light-permeable element;
   wherein an external fluid enters the round chamber via the inlet, spirally flows through an inside of the round chamber along the arc-shaped guiding channel, and flows out of the outlet after being irradiated by UV rays of the UV LED.

2. The UV sterilizing box structure of claim 1, wherein a shape of the box body is of a cylindrical shape.

3. The UV sterilizing box structure of claim 1, further comprising: a heat sink, connected to the box body and abutting against the circuit board, and the heat sink comprising a plurality of fins disposed on a side surface thereof away from the box body.

4. The UV sterilizing box structure of claim 3, wherein the heat sink comprises a heat conducting block disposed in an accommodating space thereof, and the circuit board is disposed on the heat conducting block.

5. The UV sterilizing box structure of claim 1, wherein the outlet is located on another side surface of the box body and a normal direction of the outlet is perpendicular to a normal direction of the inlet.

6. The UV sterilizing box structure of claim 1, wherein the box body comprises a recess disposed on a bottom of the round chamber, and the UV LED is located in the recess.

7. The UV sterilizing box structure of claim 6, wherein the light-permeable element comprises a light-permeable plate, and the light-permeable element is fixed on a top portion of the recess and covers the UV light module.

8. The UV sterilizing box structure of claim 1, wherein the arc-shaped guiding channel is disposed as tapering off toward the inside of the round chamber for a spiral shape.

9. The UV sterilizing box structure of claim 1, wherein the box body comprises a conic shell disposed on an opposite side from the arc-shaped guiding channel, and the outlet is disposed on the conic shell.

10. The UV sterilizing box structure of claim 9, wherein the conic shell comprises a conic chamber and a flat top, the conic chamber is communicated with the round chamber, and the outlet is located on the flat top.

* * * * *